United States Patent
Wang et al.

(10) Patent No.: US 8,821,913 B2
(45) Date of Patent: Sep. 2, 2014

(54) CONTROLLED RELEASES SYSTEM CONTAINING TEMOZOLOMIDE

(75) Inventors: Yongfeng Wang, Tianjin (CN); Dan Fei, Tianjin (CN)

(73) Assignee: Tasly Holding Group Co., Ltd., Tianjin (CN)

( * ) Notice: Subject to any disclaimer, the term of this patent is extended or adjusted under 35 U.S.C. 154(b) by 2081 days.

(21) Appl. No.: 10/529,454

(22) PCT Filed: Sep. 29, 2003

(86) PCT No.: PCT/CN03/00838
§ 371 (c)(1),
(2), (4) Date: Jun. 20, 2005

(87) PCT Pub. No.: WO2004/028534
PCT Pub. Date: Apr. 8, 2004

(65) Prior Publication Data
US 2005/0244494 A1    Nov. 3, 2005

(30) Foreign Application Priority Data
Sep. 29, 2002 (CN) .................................. 02 1 31347

(51) Int. Cl.
*A61K 9/20* (2006.01)
*A61K 9/22* (2006.01)
*A61K 31/41* (2006.01)
*A61K 9/00* (2006.01)
*A61K 31/395* (2006.01)

(52) U.S. Cl.
CPC ............... *A61K 9/0085* (2013.01); *A61K 31/41* (2013.01); *A61K 31/395* (2013.01)
USPC ............ 424/426; 424/422; 424/423; 424/468

(58) Field of Classification Search
CPC ....... A61K 9/00; A61K 9/141; A61K 9/1611; A61K 9/1635; A61K 9/1682; A61K 9/20; A61K 9/2009; A61K 9/2095
USPC .......................... 424/424, 425, 426, 489, 486
See application file for complete search history.

(56) References Cited

U.S. PATENT DOCUMENTS

| 6,086,908 A * | 7/2000 | Gopferich ..................... 424/424 |
| 6,753,014 B1 * | 6/2004 | Sjoblom ....................... 424/489 |
| 2002/0128228 A1 * | 9/2002 | Hwu .............................. 514/58 |

FOREIGN PATENT DOCUMENTS

| CN | 1156400 | 8/1997 | |
| CN | 1345240 | 4/2002 | |
| WO | WO 00/57867 A2 * | 10/2000 | ............. A61K 31/00 |
| WO | WO 0057867 A2 * | 10/2000 | |
| WO | WO 0201797 | 3/2002 | |

* cited by examiner

*Primary Examiner* — Michael G Hartley
*Assistant Examiner* — Micah-Paul Young
(74) *Attorney, Agent, or Firm* — Ballard Spahr LLP

(57) ABSTRACT

The present invention relates to a controlled release system, in particular to a controlled release system containing temozolomide.

8 Claims, 2 Drawing Sheets

CONTROLLED RELEASES SYSTEM CONTAINING TEMOZOLOMIDE

The present application claims priority to China Patent Application No. CN021313247.4, filed Sep. 29, 2002, which application is incorporated herein fully by this reference.

FIELD OF THE INVENTION

The present invention relates to a controlled release drug system, in particular to a controlled release system containing temozolomide.

BACKGROUND OF THE INVENTION

Temozolomide (TMZ), an anti-tumor drug, has broad-spectrum bioactivity of anti-tumor in the murine tumor model. Clinical studies show that TMZ possesses the activities on malignant melanoma, mycosis fungoides, and advanced glioma. In addition, it also displays a subcutaneously therapeutic effect on xenotransplantated brain tumor and lung tumor in mice. In vitro anti-tumor trials prove that TMZ has anti-tumor activity against a broad range of tumor types, including brain tumor, ovarian tumor, melanoma, and those resistant to chemotherapy using conventional drugs, such as dacarbazine, carmustine, cisplatin, doxorubicin, 5-fluorouracil, etoposide, and vinblastine.

The pharmacokinetics study in mouse model showed that, after being administered, TMZ was absorbed rapidly in vivo with a half-life time of 1.13 h (i.p.) or 1.29(p.o.). In phase I clinical trial of TMZ, it was found that it was absorbed very rapidly, reaching maximum plasma concentration within 0.7 hour and having a half-life time of 1.8 h. Also, it demonstrated good distribution to all tissues, including penetration into the blood brain barrier via kidney, lung, and liver (Brindley et al., 1986; Newland et al., 1997). But, the plasma concentration of temozolomide declines very quickly after the administration of the drug. Therefore repeated administrations are required to keep the effective drug concentration in blood, and thus bring patients with both inconvenience and agonies.

Controlled release of drug is able to release the drug at a relatively constant rate during a certain period of time. The controlled release system may be exemplified by the biodegradable implantable tablet and the non-biodegradable implantable tablet, both of which have been used for the controlled release of some drugs. However, the controlled release system for TMZ has not been reported until now.

DETAILED DESCRIPTION OF THE INVENTION

Accordingly, the main object of this invention is, obviating the inconvenience of repeated administration of temozolomide, to provide a controlled release system for temozolomide capable of keeping therapeutically effective concentration of the drug.

One aspect of the present invention relates to a controlled release system containing 3 wt %~10 wt % of temozolomide and biodegradable polymeric materials.

Another aspect of the present invention relates to a process of preparing a controlled release system containing temozolomide. The said process comprises mixing 3 wt %~10 wt % of temozolomide with the biodegradable polymeric materials.

According to the invention, the said controlled release system of the invention can be used in various dosage forms suitable for controlled delivery of temozolomide, among which implantable forms, such as implantable tablets are preferred.

According to one embodiment, this temozolomide-containing implantable tablet is prepared by a process comprising:
 a. Dissolving the polymeric materials in a solvent to give a solution of polymeric materials;
 b. Dispersing temolozomide in or mixing temolozomide with said solution of polymeric materials to produce a mixture of polymeric materials and temolozomide;
 c. Spray-drying said mixture of polymeric materials and temolozomide to obtain microspheres; and
 d. Tabletting said microspheres to obtain implantable tablets.

In step (a), the polymeric materials are selected from the group consisting of polyethylene, polypropylene, polyethylene terephthalate, plasticized polyvinyl chloride, cross-linked polyester, polycarbonate, polysulfone, polystyrene, poly(2-pentene), polymethyl methacrylate, poly (1,4-phenylene), polytetrafluoroethylene and poly(anhydride). Preferably, the polymeric material is the poly (anhydride) condensed from 1,3-bis(p-carboxyphenoxy) propane (CPP) and sebacic acid (SA) in the ratio of 20 to 80, 50 to 50, 80 to 20, 70 to 30, or 30 to 70, preferably in the ratio of 20 to 80. The solvents used to dissolve polymeric materials are those only capable of dissolving polymeric materials but not capable of dissolving or reacting with temolozomide. Suitable solvents include, for example, dichloromethane, chloroform, ethyl acetate, or acetone, preferably dichloromethane.

In step (c), in the process of spray-drying, temolozomide may be mixed with other excipients or additional stabilizers, such as buffer solutions. Preferably, the carriers are non-toxic and non-immunogenic materials, thus avoiding rejection. The suitable materials for the implants include all kinds of poly (anhydride)s.

According to another embodiment, this temozolomide-containing implantable tablet is prepared by a process comprising:
 A. Dissolving the polymeric materials in a solvent to give a solution of polymeric materials;
 B. Adding the water solution of temolozomide into said solution of polymeric materials and ultrasonic-emulsifying the resultant solution to obtain a first emulsion;
 C. Mixing said first emulsion with polyvinyl alcohol (PVA), followed by evaporating the solvent to obtain hard microspheres;
 D. Eliminating PVA and residual solvent by washing with water to obtain microspheres; and
 E. Tabletting said microspheres to obtain implantable tablets.

In step (A), the polymeric materials are selected from the group consisting of polyethylene, polypropylene, polyethylene terephthalate, plasticized polyvinyl chloride, cross-linked polyester, polycarbonate, polysulfone, polystyrene, poly(2-pentene), polymethyl methacrylate, poly(1,4-phenylene), polytetrafluoroethylene, and poly(anhydride). Preferably, the polymeric material is the poly(anhydride) condensed from CPP and SA in the ratio of 20 to 80, 50 to 50, 80 to 20, 70 to 30, or 30 to 70, preferably in the ratio of 20 to 80. The solvents used to dissolve polymeric materials are those only capable of dissolving polymeric materials but not capable of dissolving or reacting with temolozomide. For example, suitable solvents include dichloromethane, chloroform, ethyl acetate, or acetone, preferably dichloromethane.

The polymer formed by CPP and SA is present in dichloromethane in the concentration ranging from 1% to 5%, preferably 2%.

In step (B), the ratio by volume of temozolomide water solution to that of the organic solvent is 1:100 to 1:400, preferably 1:100.

The said biodegradable polymeric materials used in the present invention, for example "poly(anhydride)", are known in the art and may be commercially available or produced by using a well-known method in the art.

Said temozolomide-containing controlled release system produce by the above-mentioned processes may be in the form of a sheet, a microsphere, a cylinder, a flake, etc.

The temolozomide implant tablets of the present invention may be implanted into the body of human or other animals surgically or may be implanted via non-systematic administration, for example, subcutaneously, intracranially, vaginally, intramuscularly or sub-skin to deliver therapeutically-effective amount of the drug for the treatment of diseases. The implants' dosage is determined depending on the severity of said diseases as well as weight, age and gender of the patient.

The controlled release system of the present invention are capable of delivering therapeutically-effective amount of temolozomide constantly. Accordingly, the implants are capable of releasing temozolomide in a controlled manner in vivo during a long period of time varying from 1 hour to 4 weeks, so as to result in the therapeutic effect of the drug. Consequently, the bioactivity of temolozomide can be achieved to the most extent by using the controlled release system of the present invention.

In addition, temolozomide implants of the present invention may be prepared by using various carriers. In general, the implants are degraded after about 30 days from the day of being implanted and the poly(anhydride) materials are degraded after about 6 to 8 weeks from the day of being implanted.

BEST MODES FOR CARRYING OUT THE INVENTION

Figure 1:
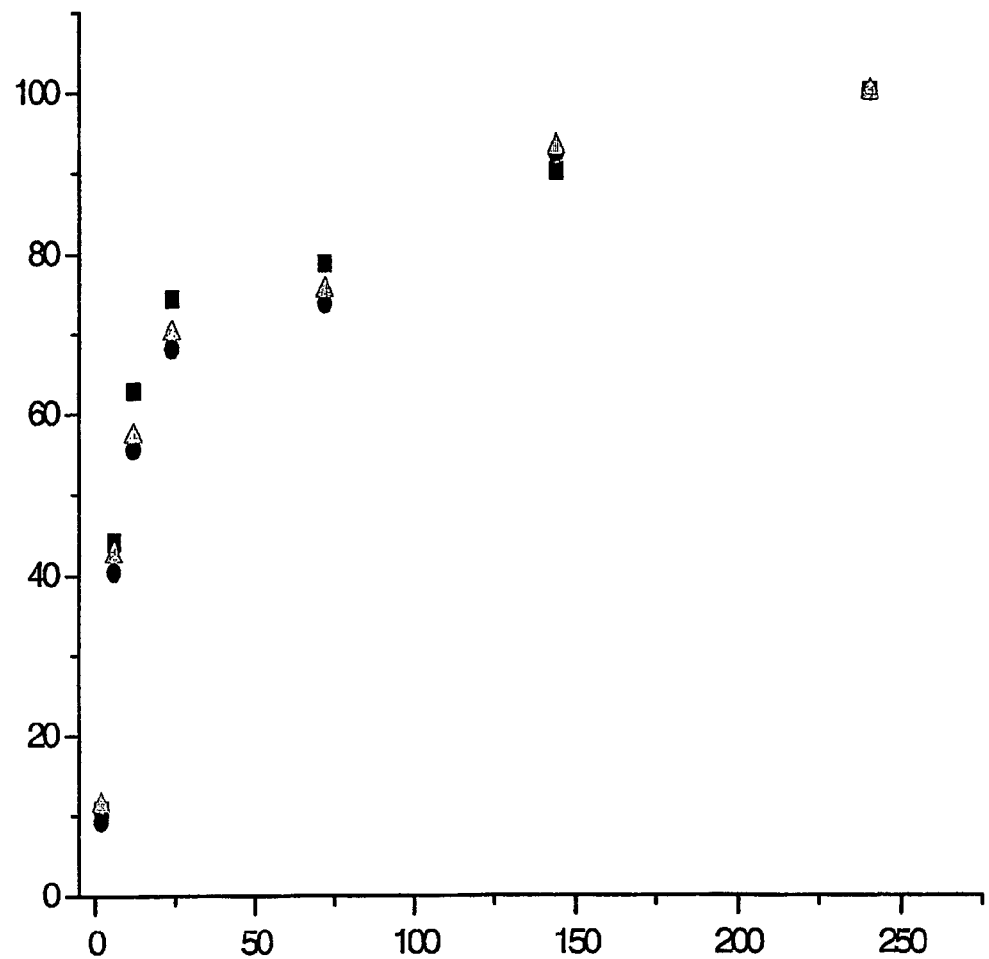
FIG. 1 is a graph showing release of implantable tablets of temolozomide in vivo, of which the black block "■" shows the implants containing 3 wt % of temozolomide, the circle "●" 5 wt % of temozolomide, and the triangle "▲" 10 wt % of temozolomide. The ordinate represents the accumulative amount of releasing (%); the abscissa denotes time (hour).
Figure 2:
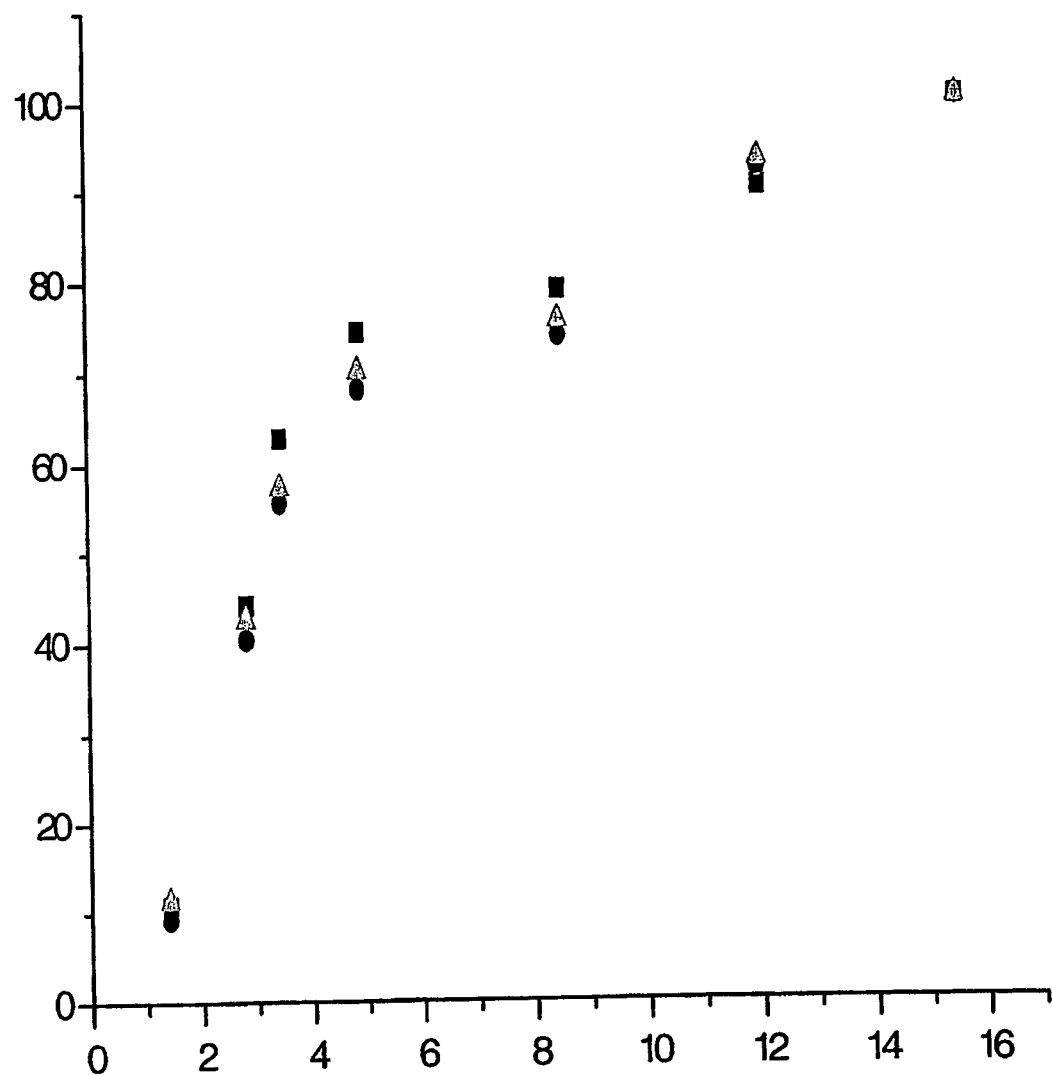
FIG. 2 is a graph of implantable tablets of temolozmide to a square root of time, of which the black block "■" shows the implants containing 3 wt % of temozolomide, the circle "●" 5 wt % of temozolomide, and the triangle "▲" 10 wt % of temozolomide. The ordinate represents an accumulative amount of releasing (%); the abscissa denotes the square root of time.

Following examples are merely intended to describe the present invention, but not to limit the scope of the application.

EXAMPLE 1

Implants Containing 3 wt % of temozolomide 97 g of biodegradable polyanhydride was prepared by mixing 1,3-bis(p-carboxyphenoxy) propane (CPP) and sebacic acid (SA) at the ratio of 20 to 80.3 g of temozolomide was added to the obtained polyanhydride. The two were mixed in methylene chloride at room temperature and sprayed to give sustained release microspheres containing 3% of temozolomide. The residual methylene chloride was evaporated under vacuum.

The conditions of spray drying were as follows: the inlet temperature of 70° C., the outlet temperature of 65° C., and the spraying pressure of 15 p.s.i.

According to the desired diameter of the implants and the dosage of temozolomide, a suitable amount of microspheres were tabletted in the mould under the pressure of 8000 p.s.i in five seconds to produce the implant tablets containing 3 wt % of temozolomide, having the diameter of 1.4 cm and the thickness of 1.0 mm. The said implant tablets were sealed into the aluminum laminated plastic under nitrogen before disinfected with gamma ray at 2.2*10 Gy.

EXAMPLE 2

99 g of biodegradable polyanhydride was prepared by mixing 1,3-bis(p-carboxyphenoxy) propane (CPP) and sebacic acid (SA) at the ratio of 80 to 20.1 g of temozolomide was added to the obtained polyanhydride. The two were mixed in chloroform at room temperature and sprayed to give sustained release microspheres containing 1 wt % of temozolomide. The residual methylene chloride was evaporated under vacuum.

The conditions of spray drying were as follows: the inlet temperature of 75° C., the outlet temperature of 70° C., and the spraying pressure of 15 p.s.i.

According to the desired diameter of the implants and the dosage of temozolomide, a suitable amount of microspheres were tabletted in the mould under the pressure of 8000 p.s.i in five seconds to produce the implant tablets containing 1 wt % of temozolomide, having the diameter of 1.4 cm and the thickness of 1.0 mm. The said implant tablets were sealed into the aluminum laminated plastic under nitrogen before disinfected with gamma ray at 2.2*10 Gy.

EXAMPLE 3

90 g of biodegradable polyanhydride was prepared by mixing 1,3-bis(p-carboxyphenoxy) propane (CPP) and sebacic acid (SA) at the ratio of 30 to 70.10 g of temozolomide was added to the obtained polyanhydride. The two were mixed in ethyl acetate at room temperature and sprayed to give sustained release microspheres containing 10 wt % of temozolomide. The residual methylene chloride was evaporated under vacuum.

The conditions of spray drying were as follows: the inlet temperature of 70° C., the outlet temperature of 65° C., and the spraying pressure of 15 p.s.i.

According to the desired diameter of the implants and the dosage of temozolomide, a suitable amount of microspheres were tabletted in the mould under the pressure of 8000 p.s.i in five seconds to produce the implant tablets containing 10 wt % of temozolomide, having the diameter of 1.4 cm and the thickness of 1.0 mm. The said implant tablets were sealed into the aluminum laminated plastic under nitrogen before disinfected with gamma ray at 2.2*10 Gy.

EXAMPLE 4

95 g of biodegradable polyanhydride was prepared by mixing 1,3-bis(p-carboxyphenoxy) propane (CPP) and sebacic acid (SA) at the ratio of 70 to 30.5 g of temozolomide was added to the obtained polyanhydride. The two were mixed in methylene chloride at room temperature and sprayed to give sustained release microspheres containing 5 wt % of temozolomide. The residual methylene chloride was evaporated under vacuum.

The conditions of spray drying were as follows: the inlet temperature of 75° C., the outlet temperature of 60° C., and the spraying pressure of 15 p.s.i.

According to the desired diameter of the implants and the dosage of temozolomide, a suitable amount of microspheres were tabletted in the mould under the pressure of 8000 p.s.i in five seconds to produce the implant tablets containing 5 wt % of temozolomide, having the diameter of 1.4 cm and the thickness of 1.0 mm. The said implant tablets were sealed into the aluminum laminated plastic under nitrogen before disinfected with gamma ray at 2.2*10 Gy.

EXAMPLE 5

95 g of biodegradable polyanhydride was prepared by mixing 1,3-bis(p-carboxyphenoxy) propane (CPP) and sebacic acid (SA) at the ratio of 50 to 50.5 g of temozolomide was added to the obtained polyanhydride. The two were mixed in methylene chloride at room temperature and sprayed to give sustained release microspheres containing 5 wt % of temozolomide. The residual methylene chloride was evaporated under vacuum.

The conditions of spray drying were as follows: the inlet temperature of 65° C., the outlet temperature of 60° C., and the spraying pressure of 15 p.s.i.

According to the desired diameter of the implants and the dosage of temozolomide, a suitable amount of microspheres were tabletted in the mould under the pressure of 8000 p.s.i in five seconds to produce the implant tablets containing 5 wt % of temozolomide, having the diameter of 1.4 cm and the thickness of 1.0 mm. The said implant tablets were sealed into the aluminum laminated plastic under nitrogen before disinfected with gamma ray at 2.2*1.0 Gy.

EXAMPLE 6

Copolymer of CPP and SA at the ratio of 20 to 80 was dissolved in methylene chloride to give the solution of 2% (w/v) at room temperature, into which suitable amount of water solution of temozolomide was added. After being mixed well, the mixture was ultrasonic-emulsified to produce a w/o first emulsion. The first emulstion was mixed with a water solution of 2% polyvinyl alchohol (PVA) in high speed to form the emulsion. This emulsion was poured into water solution of 0.1% PVA, and stirred for four hours at room temperature. The solvent methylene chloride was evaporated at room temperature, and hard microspheres appeared in the water solution of PVA. The microspheres were washed with di-distilled water for three times to eliminate the residual methylene chloride and PVA and freeze-dried to obtain the microspheres containing 4 wt % temozolomide and having a diameter of about 20 micrometer with good fluidity.

According to the desired diameter of the implants and the dosage of temozolomide, a suitable amount of microspheres were tabletted in the mould under the pressure of 8000 p.s.i in five seconds to produce the implant tablets containing 4 wt % of temozolomide, having the diameter of 1.4 cm and the thickness of 1.0 mm. The said implant tablets were sealed into the aluminum laminated plastic under nitrogen and disinfected with gamma ray at 2.2*10 Gy.

EXAMPLE 7

Copolymer of CPP and SA at the ratio of 80 to 20 was dissolved in ethyl acetate to give the solution of 1% (w/v) at room temperature, into which suitable amount of water solution of temozolomide was added. After being mixed well, the mixture was ultrasonic-emulsified to produce a w/o first emulsion. The first emulsion was mixed with a water solution of 2% PVA in high speed to form the emulsion. This emulsion was poured into water solution of 0.1% PVA, and stirred for four hours at room temperature. The solvent ethyl acetate was evaporated at room temperature, and hard microspheres appeared in the water solution of PVA. The microspheres were washed with di-distilled water for three times to eliminated the residual methylene chloride and PVA and freeze-dried to obtain the microspheres containing 6 wt % temozolomide and having a diameter of about 20 micrometer with good fluidity.

According to the desired diameter of the implants and the dosage of temozolomide, a suitable amount of microspheres were tabletted in the mould under the pressure of 8000 p.s.i in five seconds to produce the implant tablets containing 6 wt % of temozolomide, having the diameter of 1.4 cm and the thickness of 1.0 mm. The said implant tablets were sealed into the aluminum laminated plastic under nitrogen and disinfected with gamma ray at 2.2*10 Gy.

EXAMPLE 8

Copolymer of CPP and SA at the ratio of 50 to 50 was dissolved in chloroform to give the solution of 5% (w/v) at room temperature, into which suitable amount of water solution of temozolomide was added. After being mixed well, the mixture was ultrasonic-emulsified to produce a w/o first emulsion. The first emulsion was mixed with a water solution of 2% PVA in high speed to form the emulsion. This emulsion was poured into water solution of 0.1% PVA, and stirred for four hours at room temperature. The solvent chloroform was evaporated at room temperature, and hard microspheres appeared in the water solution of PVA. The microspheres were washed with di-distilled water for three times to eliminate the residual methylene chloride and PVA and freeze-dried to obtain the microspheres containing 6 wt % of temozolomide and having a diameter of about 20 micrometer with good fluidity.

According to the desired diameter of the implants and the dosage of temozolomide, a suitable amount of microspheres were tabletted in the mould under the pressure of 8000 p.s.i in five seconds to produce the implant tablets containing 6 wt % of temozolomide, having the diameter of 1.4 cm and the thickness of 1.0 mm. The said implant tablets were sealed into the aluminum laminated plastic under nitrogen and disinfected with gamma ray at 2.2*10 Gy.

TEST EXAMPLE

Kinetics of Temolozomide Release from Implantable Tablets in Animals

The characteristics of dynamic changes of temolozomide release from implantable tablets in animals were determined in this study, so as to provide a reference for rational clinical use of this drug.

Materials

1. Apparatus and Reagents

Agilent 1100 High Performance Liquid Chromatograph, ODS reverse phase chromatographic column (Supelcolc-C18 column, 250 mm×4.6 mm, 5 um), and DAD detector were used. Both standard temolozomide reference and implants (produced by the process in example 1) were provided by Tianjin Tasly Group. The methanol, acetic acid and ethyl acetate were chromatographic grade.

2. Animals: Male Wister rats, weighing from 200 to 250 g, were obtained from the Animal Center of Tianjin Medical University.

Methodology

1. Erosion and release of temolozomide implants in the cerebrum of rats Seventy rats were randomly assigned to four groups, twenty-one rats each in three groups, and seven ones, in the fourth group. Before surgical procedure, every rat was anesthetized, shaved, and disinfected with ethanol and tinctura iodi. A 2-cm incision was made along midline, and then, by using bur, drilling was performed at the point 5-6 mm to rear coronal suture and 3 mm to unilateral sagittal suture. A 4-mm-deep nicking was produced by a microsurgical knife on the cortex, into which the implant tablets with 3%, 5% and 10% of temolozomide were inserted in the first three groups, and a blank polymer tablet in the fourth group. After blood being stopped completely, the burr holes were sealed with bone wax; the wounds were cleaned with saline and clamped with operation clamps.

Three rats in each of the first three groups and one rat in the fourth were sacrificed in succession at 2, 6, 12 hour and 1, 3, 6, 10 day after implants being inserted. The implant tablets were separately taken out of the brains, and freeze-dried in dry ice. The active agent temozolomide in the implants was determined by High Performance Liquid Chromatography (HPLC).

2. The Extraction of Temozolomide

Both the temozolomide implant tablets of three different concentrations and the blank one were withdrawn from the brain of rats at the scheduled time points. After freeze-drying, the residual tablets were placed into a mobile phase of 2 ml, ultrasonicated for 5 min to dissolve them completely, and ultracentrifuged for 5 min at 4000 rpm before a supernate of 10 μL was removed for analysis.

3. Determination of Temozolomide

Agilent 1100 HPLC equipped with an ODS reverse phase column (Supelcolc-C18 column, 250 mm×4.6 mm, 5 um) and a DAD detector having the minimum detection limit of 0.1 mg/ml was used with the chromatographic condition as follows: methanol-0.5% acetic acid (10:90) as the mobile phase at the flow rate of 1 ml/min, and the detection wavelength 330 nm. The temoilozomide implant tablets were extracted with ethyl acetate.

4. The in vivo Release Quantity of Temolozomide

Accumulative release quantity =

$$\frac{\text{average concentration of temolozomide in the implant tablets} - \text{average concentration in the withdrawn ones}}{\text{Average concentration of temolozomide in the implant tablets}} \times 100\%$$

5. Establishment of Standard Curve

The standard solutions of 100 μg/ml temolozomide in the amount of 5, 10, 30, 100, 200, 300, and 400 μL were respectively dispensed into centrifuge tubes, and dried under nitrogen stream. The blank tablets were added and extracted in the same way as the temolozomide tablets to give a series of temolozomide standard solutions having the concentration of 0.25, 0.5, 1.5, 2.5, 3.5, 5.0, 10.0, 15.0, or 20.0 μg/ml respectively. 10 μL of the supernate was subsequently injected into the HPLC to measure peak area. A concentration(C)-peak area(A) curve was constructed to calculate linear regression equation.

Result

1. Erosion and release of temolozomide implant in brain were shown in FIG. 1.

TABLE 1

Percentages of average accumulative releases of temolozomide implant in brain in rats ($\bar{x} \pm S$, n = 3)

| | 2 h (%) | 6 h (%) | 12 h (%) | 1 d (%) | 3 d (%) | 6 d (%) | 10 d (%) |
|---|---|---|---|---|---|---|---|
| Group of 3% implant | 9.27 ± 0.38 | 40.37 ± 2.15 | 55.54 ± 3.53 | 68.13 ± 4.12 | 73.82 ± 5.82 | 92.17 ± 6.42 | 100 ± 2.58 |
| Group of 5% implant | 11.36 ± 0.57 | 42.51 ± 3.38 | 57.29 ± 5.34 | 70.14 ± 3.69 | 75.47 ± 4.79 | 93.11 ± 5.58 | 99.85 ± 3.72 |
| Group of 10% implant | 10.73 ± 0.63 | 44.18 ± 2.65 | 62.83 ± 4.17 | 74.38 ± 6.13 | 78.89 ± 6.33 | 90.05 ± 7.32 | 100 ± 4.29 |

2. The results of HPLC showed that standard curve was in good linearity over the range of 0.4~20 μg/ml.

$Y=79.4810+14182.0760x$, $r=0.9999$

CONCLUSION

This test showed that temolozomide could be slowly released from the implant tablets. From the graph of release to square-root of time, it was clear that good linearity was present in the early stage after implantation of temozolomide implants, showing that the whole course of implants' degradation had two distinct stages, induction stage and erosion stage. The free temozolomide started to release from the implants within one hour after implantation. The temozolomide implants in the brains of rats could keep releasing the drug over ten days.

The invention claimed is:

1. A controlled release system, consisting essentially of 4-10 wt % of temozolomide and biodegradable polyanhydrides, wherein the polyanhydrides are condensed from 1,3-bis(p-carboxyphenoxy) propane (CPP) and sebacic acid (SA), wherein the controlled release system releases temozolomide for a period ranging from 6 hours to 4 weeks in vivo.

2. The controlled release system according to claim 1, which is an implantable tablet.

3. A process of preparing temozolomide controlled release tablets, comprising:
   a. Dissolving polyanhydrides in a solvent to give a solution of polyanhydrides, wherein the polyanhydrides are condensed from 1,3-bis(p-carboxyphenoxy) propane (CPP) and sebacic acid (SA);
   b. Dispersing temolozomide in or mixing temolozomide with the solution of polyanhydrides to produce a mixture of polyanhydrides and temolozomide;
   c. Spray-drying the mixture of polyanhydrides and temolozomide to obtain microspheres; and
   d. Tabletting the microspheres to obtain implantable tablets;
   wherein the controlled release system releases temozolomide for a period ranging from 6 hours to 4 weeks in vivo.

4. The process according to claim 3, wherein the solvent in step (a) is methylene chloride.

5. A process of preparing temozolomide controlled release tablets, comprising:
   a. Dissolving polyanhydrides in a solvent to give a solution of polyanhydrides, wherein the polyanhydrides are condensed from 1,3-bis(p-carboxyphenoxy) propane (CPP) and sebacic acid (SA);
   b. Adding temolozomide into the solution of polyanhydrides and ultrasonic-emulsifying the resultant solution to obtain a first emulsion;
   c. Mixing the first emulsion with polyvinyl alcohol (PVA), followed by evaporating the solvent to obtain hard microspheres;
   d. Eliminating PVA and residual solvent by washing with water to obtain microspheres; and
   e. Tabletting the microspheres to obtain implantable tablets;

wherein said controlled release system releases temozolomide for a period ranging from 6 hours to 4 weeks in vivo.

6. The process according to claim 5, wherein the solvent in step (a) is methylene chloride.

7. The process according to claim 3, wherein the resultant controlled release system consists essentially of temozolomide and biodegradable polyanhydrides.

8. The process according to claim 5, wherein the resultant controlled release system consists essentially of temozolomide and biodegradable polyanhydrides.

\* \* \* \* \*